United States Patent [19]

Dygos et al.

[11] 4,008,257
[45] Feb. 15, 1977

[54] 2,2-DIMETHYL-2-[(7,15,16,17-TETRAHYDRO-17,17-DIMETHYL-6H-CYCLOPENTA[a]PHENANTHREN-3-YL)OXY]ETHYL ALKANEDIOATES AND INTERMEDIATES THERETO

[75] Inventors: John H. Dygos, Northbrook; Karlene W. Salamon, Chicago, both of Ill.

[73] Assignee: G. D. Searle & Co., Chicago, Ill.

[22] Filed: Mar. 10, 1976

[21] Appl. No.: 665,362

[52] U.S. Cl. .......................... 260/397.1; 260/397.5
[51] Int. Cl.$^2$ ......................................... C07J 9/00
[58] Field of Search ................................ 260/397.1

[56] References Cited

UNITED STATES PATENTS

| | | | |
|---|---|---|---|
| 3,769,306 | 10/1973 | Kuo et al. | 260/397.1 |
| 3,933,870 | 1/1976 | Cohen | 260/397.5 |

*Primary Examiner*—Elbert L. Roberts
*Attorney, Agent, or Firm*—John M. Brown

[57] ABSTRACT

Preparation and the antihypercholesterolemic activity of 2,2-dimethyl-2-[(7,15,16,17-tetrahydro-17,17-dimethyl-6H-cyclopental[a]phenanthren-3-yl)oxy] ethyl alkanedioates and intermediates thereto are disclosed.

6 Claims, No Drawings

2,2-DIMETHYL-2-[(7,15,16,17-TETRAHYDRO-17,17-DIMETHYL-6H-CYCLOPENTA[a]PHENANTHREN-3-YL)OXY]ETHYL ALKANEDIOATES AND INTERMEDIATES THERETO

This invention relates to 2,2-dimethyl-2-[(7,15,16,17-tetrahydro-17,17-dimethyl-6H-cyclopenta [a]phenanthren-3-yl)oxy]ethyl alkanedioates and intermediates thereto. More particularly, this invention provides new, useful, and unobvious steroids of the formula

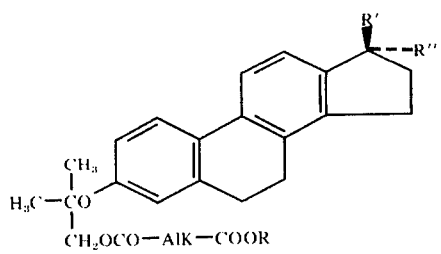

wherein R, R', and R'' each represent hydrogen or alkyl and Alk represents alkylene. Among the alkyls represented by R, R', and R'' in the foregoing formula, lower alkyls are preferred, which is to say methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, and like monovalent, saturated, acyclic, straight- or branched-chain, hydrocarbon groupings of the formula

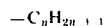

wherein $n$ represents a positive integer less than 8. Especially preferred embodiments of R' and R'' are methyls.

The alkylenes comprehended by Alk in the introductory formula, like the alkyls called for by R, R', and R'' therein, are preferably of lower order also, for example, 1,2-ethanediyl, 1-methyl-1,2-ethanediyl, 1,1-dimethyl-1,2-ethanediyl, 1,1-propanediyl, 2,2-dimethyl-1,3-propanediyl, 1,4-butanediyl, or such bivalent, saturated, acyclic, straight- or branched-chain, hydrocarbon grouping of the formula

wherein $n$ is defined as before. Among these lower alkylenes, 1,2-ethanediyl and 1,3-propanediyl are especially preferred.

The compounds to which this invention relates are useful by reason of their valuable biological properties. Thus, for example, they are antihypercholesterolemic: In the standardized test for such utility described in U.S. Pat. No. 3,501,506, the products of Examples 1D and 2 hereinafter lowered cholesterol levels, relative to controls, by 17 and 7%, respectively, at doses of 10 mg/kg, administered intragastrically. The intermediates thereto described in Examples 1A, 1B, and 1C likewise lowered cholesterol by 10, 18, and 24% at intragastric doses of 20, 15, and 10 mg/kg, respectively, in the aforesaid test. The antihypercholesterolemic activity of the product of Example 1D is especially interesting because it was unaccompanied by the slight estrogenicity which characterized other compounds of this invention tested via the standardized procedure described in U.S. Pat. No. 3,501,506.

Those skilled in the art will recognize that observations of activity in standardized tests for particular biological effects are fundamental to the development of valuable new drugs, both veterinary and human.

Preparation of the compounds of this invention proceeds by heating an ether of the formula

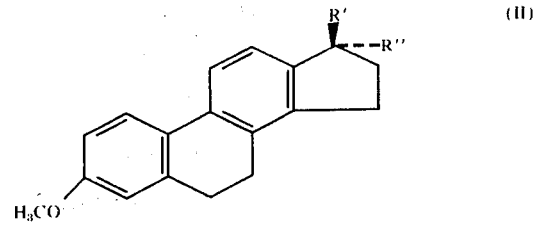

with pyridine hydrochloride under nitrogen to cleave the methoxyl therein; heating a toluene solution of the phenol thus obtained with a mineral oil dispersion of sodium hydride and heating the resultant sodium salt in situ under nitrogen with 2-bromo-2-methylpropanoic acid to produce a 2-methyl-2-[(7,15,16,17-tetrahydro-6H-cyclopenta [a]phenanthren-3-yl)oxy]propanoic acid of the formula

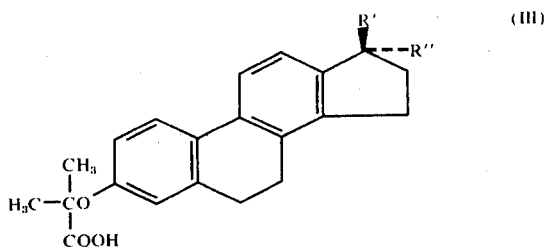

in which the carboxyl is reduced by contacting the acid with lithium tetrahydroaluminate (1-) in tetrahydrofuran; and contacting the 2-methyl-2-[(7,15,16,17-tetrahydro-6H-cyclopenta [a]phenanthren-3-yl)oxy]-1-propanol which eventuates, under nitrogen, with an alkyl ω-chloro-ω-oxoalkanoate in pyridine. The product, an ester of the formula

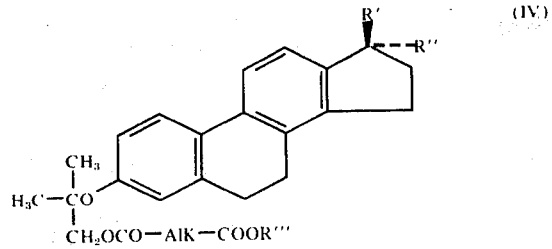

in which R''' has the meaning previously assigned to R except that it does not represent hydrogen, is heated with lithium iodide in pyridine at the boiling point under nitrogen to cleave the alkoxyl therein, affording a corresponding product of the formula

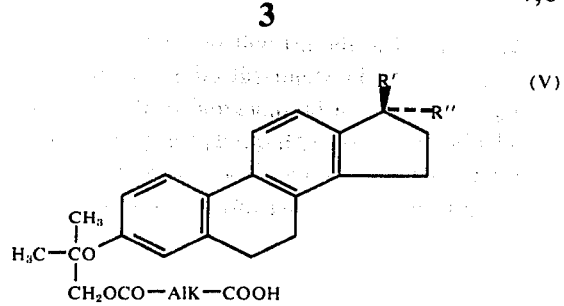

Wherever they appear in the four formulas immediately preceding, R', R'', and Alk are defined as before.

An alternative route to an ester of Formula IV hereinbefore is esterification of an acid of Formula V via contact with just sufficient methanolic potassium hydroxide to form the potassium salt, which in turn is contacted with an alkyl iodide (optionally in the presence of potassium bicarbonate), using N,N-dimethylformamide as the reaction medium.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. A mixture of 26 parts of 7,15,16,17-tetrahydro-3-methoxy-17,17-dimethyl-6H-cyclopenta[a]phenanthrene (Bull. soc. chim. France, 1968, 4886) and 150 parts of freshly-fused pyridine hydrochloride is heated in an atmosphere of nirogen at 220° for 1 ½ hours. The reaction mixture is then poured into 200 parts of water, whereupon insoluble solids are filtered out, washed with water, dried in air, and crystallized from a mixture of ether and hexane to give 7,15,16,17-tetrahydro-17,17-dimethyl-6H-cyclopenta[a]phenanthren-3-ol melting at approximately 152°–153°, and having the formula

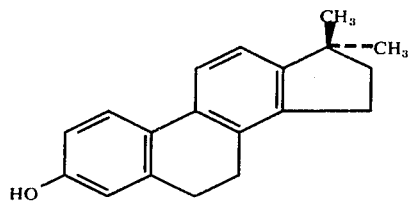

B. To a solution of 19 parts of 7,15,16,17-tetrahydro-17,17-dimethyl-6H-cyclopenta[a]phenanthren-3-ol in 800 parts of toluene is added 13 parts of a 50% dispersion of sodium hydride in mineral oil. The resultant mixture is stirred and heated at the boiling point under reflux in an atmosphere of nitrogen for 1 hour, then cooled, whereupon approximately 13 parts 2-bromo-2-methylpropanoic acid is introduced. The mixture thus obtained is stirred and heated at the boiling point under reflux in a nitrogen atmosphere for 4 hours, at which point heating is discontinued. The mixture is stirred 18 hours longer at ambient temperatures, then approximately 250 parts of water is cautiously introduced. The mixture so produced is extracted with benzene. The benzene extract is washed with water, dried over anhydrous sodium sulfate, and stripped of solvent by vacuum distillation. Crystallization of the residue from a mixture of ether and hexane affords 2-methyl-2-[(7,15,16,17-tetrahydro-17,17-dimethyl-6H-cyclopenta[a]phenanthren-3-yl)oxy]propanoic acid melting at 167°–170°, and having the formula

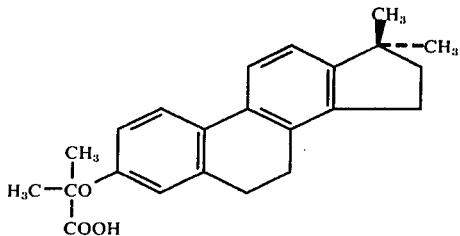

C. To a solution of 17 parts of lithium tetrahydroaluminate(1-) in 360 parts of tetrahydrofuran is slowly added a solution of 47 parts of 2-methyl-2-[(7,15,16,17-tetrahydro-17,17-dimethyl-6H-cyclopenta[a]phanthren-3-yl)oxy]propanoic acid in 720 parts of tetrahydrofuran. The resultant mixture is stirred at room temperatures for 16 hours, then consecutively diluted with 180 parts of ethyl acetate and 100 parts of water. The mixture thus obtained is extracted with ethyl acetate. The extract is consecutively washed with aqueous 10% potassium hydroxide and water, dried over anhydrous sodium sulfate, and stripped of solvent by vacuum distillation. Crystallization of the residue from a mixture of dichloromethane and hexane affords 2-methyl-2-[(7,15,16,17-tetrahydro-17,17-dimethyl-6H-cyclopenta[a]phenanthren-3-yl)oxy]-1-propanol melting at 122°–125°. It has the formula

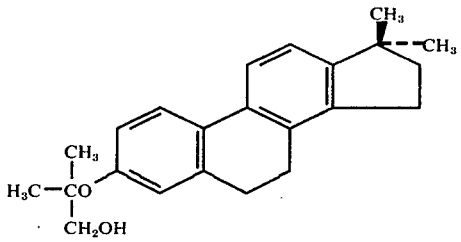

D. To a solution of 22 parts of 2-methyl-2-[(7,15,16,17-tetrahydro-17,17-dimethyl-6H-cyclopenta[a]-phenanthren-3-yl)oxy]-1-propanol in 900 parts of pyridine under nitrogen at 0°–5° is slowly added 130 parts of methyl 4-chloro-4-oxobutanoate. The resultant mixture is stirred vigorously at room temperatures for 3 hours, then poured into 3 volumes of water. The mixture thus obtained is extracted with ethyl acetate. The extract is washed with water, dried over anhydrous sodium sulfate, and stripped of solvent by vacuum distillation. The residue is taken up in benzene, and the benzene solution is chromatographed on silica gel. Elution with a 10% solution of ethyl acetate in benzene and removal of the solvent from the eluate via vacuum distillation leaves a residue which, crystallized from methanol, affords methyl 2,2-dimethyl-2-[(7,15,16,17-tetrahydro-17,17-dimethyl-6H-cyclopenta[a]phenanthren-3-yl)oxy]ethyl butanedioate melting at 58°–60°. The product has the formula

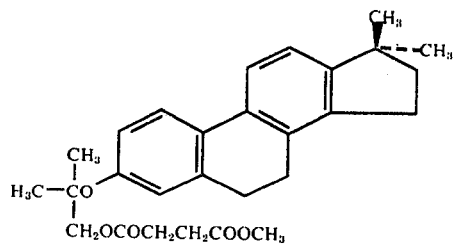

EXAMPLE 2

A mixture of 7 parts of methyl 2,2-dimethyl-2-[(7,15,16,17-tetrahydro-17,17-dimethyl-6H-cyclopenta[a]phenanthren-3-yl)oxy]ethyl butanedioate and 24 parts of lithium iodide in 700 parts of pyridine is heated at the boiling point under reflux for 3 days, then cooled and thereupon poured into 1000 parts of approximately 4% hydrochloric acid. The resultant mixture is extracted with dichloromethane. The dichloromethane extract is consecutively washed with 4% hydrochloric acid and water, dried over anhydrous sodium sulfate, and stripped of solvent by vacuum distillation. The residue is crystallized from a mixture of ether and hexane to give 2,2-dimethyl-2-[(7,15,16,17-tetrahydro-17,17-dimethyl-6H-cyclopenta[a]phenanthren-3-yl)oxy]ethyl hydrogen butanedioate melting at 118°–120°. The product has the formula

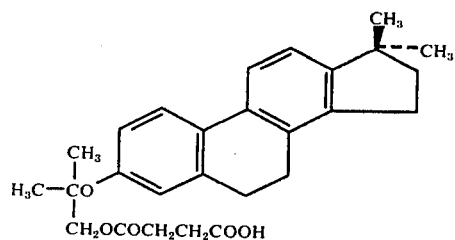

EXAMPLE 3

Substitution of 142 parts of ethyl 4-chloro-4-oxobutanoate for the methyl 4-chloro-4-oxobutanoate called for in Example 1D affords, by the procedure there detailed, ethyl 2,2-dimethyl-2-[(7,15,16,17-tetrahydro-17,17-dimethyl-6H-cyclopenta[a]phenanthren-3-yl)oxy]ethyl butanedioate.

EXAMPLE 4

Substitution of 142 parts of methyl 5-chloro-5-oxopentanoate for the methyl 4-chloro-4-oxobutaneoate called for in Example 1D affords, by the procedure there detailed, methyl 2,2-dimethyl-2-[(7,15,16,17-tetrahydro-17,17-dimethyl-6H-cyclopenta[a]phenanthren-3-yl)oxy]ethyl pentanedioate. The product has the formula

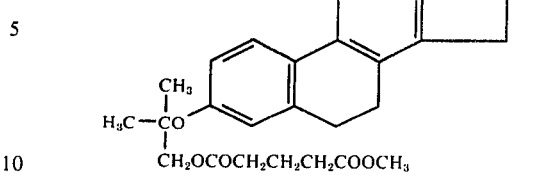

EXAMPLE 5

To a solution of 436 parts of 2,2-dimethyl-2-[(7,15,16,17-tetrahydro-17,17-dimethyl-6H-cyclopenta[a]phenanthren-3-yl)oxy]ethyl hydrogen butanedioate in 3200 parts of methanol is slowly added a solution of 59 parts of potassium hydroxide in 1000 parts of water. The resultant mixture is stirred for 15 minutes, whereupon solvents are removed by vacuum distillation. The residue is suspended in 4000 parts of N,N-dimethylformamide. To this suspension is added 8500 parts of 2-methylethyl iodide and 100 parts of potassium bicarbonate. The mixture thus obtained is stirred for 18 hours and then diluted with 3 volumes of water. The resultant mixture is extracted with benzene. The benzene extract is washed with water, dried over anhydrous sodium sulfate, and stripped of solvent by vacuum distillation. The residue is 2-methylethyl 2,2-dimethyl-2-[(7,15,16,17-tetrahydro-17,17-dimethyl-6H-cyclopenta[a]-phenanthren-3-yl)oxy]ethyl butanedioate.

What is claimed is:

1. A compound of the formula

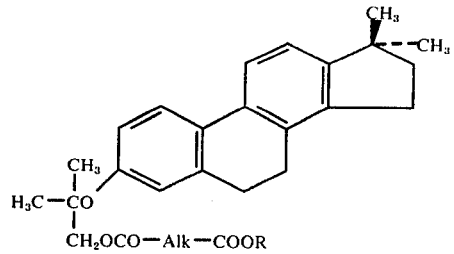

wherein Alk represents 1,2-ethanediyl or 1,3-propanediyl and R represents hydrogen or alkyl containing fewer than 8 carbons.

2. A compound according to claim 1 having the formula

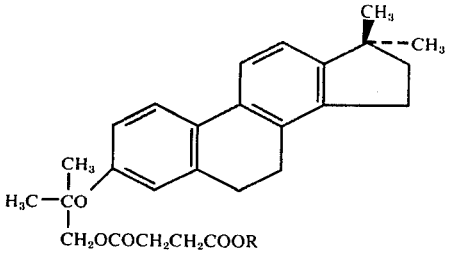

wherein R represents alkyl containing fewer than 8 carbons.

3. A compound according to claim 1 which is methyl 2,2-dimethyl-2-[(7,15,16,17-tetrahydro-17,17-dimethyl-6H-cyclopenta[a]phenanthren-3-yl)oxy]ethyl butanedioate.

4. A compound according to claim 1 which is 2,2-dimethyl-2-[(7,15,16,17-tetrahydro-17,17-dimethyl-6H-cyclopenta[a]phenanthren-3-yl)oxy]ethyl hydrogen butanedioate.

5. A compound according to claim 1 which is 2-methyl-2-[(7,15,16,17-tetrahydro-17,17-dimethyl-6H-cyclopenta[a]phenanthren-3-yl)oxy]propanoic acid.

6. A compound according to claim 1 which is 2-methyl-2-[(7,15,16,17-tetrahydro-17,17-dimethyl-6H-cyclopenta[a]phenanthren-3-yl)oxy]-1-propanol.

* * * * *